(12) United States Patent
Van Der Linde et al.

(10) Patent No.: US 10,821,265 B2
(45) Date of Patent: Nov. 3, 2020

(54) STEERABLE MEDICAL DEVICE, AND USE OF A PULL WIRE RING THEREIN

(71) Applicant: KONINKLIJKE PHILIPS N.V., Eindhoven (NL)

(72) Inventors: Franciscus Reinier Antonius Van Der Linde, Schijndel (NL); Franciscus Johannes Gerardus Hakkens, Eindhoven (NL); Cornelis Gerardus Maria De Haas, Nuenen (NL); Cornelius Antonius Nicolaas Maria Van Der Vleuten, Liempde (NL); Adrianus Wilhelmus Dionisius Maria Van Den Bijgaart, Helvoirt (NL); Maurice Hubertus Elisabeth Van Der Beek, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 460 days.

(21) Appl. No.: 15/523,963

(22) PCT Filed: Nov. 4, 2015

(86) PCT No.: PCT/EP2015/075660
§ 371 (c)(1),
(2) Date: May 3, 2017

(87) PCT Pub. No.: WO2016/071378
PCT Pub. Date: May 12, 2016

(65) Prior Publication Data
US 2017/0361066 A1     Dec. 21, 2017

(30) Foreign Application Priority Data
Nov. 4, 2014  (EP) .................................... 14191734

(51) Int. Cl.
*A61M 25/01* (2006.01)
*A61M 25/09* (2006.01)

(52) U.S. Cl.
CPC .... *A61M 25/0147* (2013.01); *A61M 25/0158* (2013.01); *A61M 25/09* (2013.01); *A61M 2025/0166* (2013.01)

(58) Field of Classification Search
CPC ............... A61B 1/0057; A61B 1/0008; A61B 2017/00305; A61B 2017/00323;
(Continued)

(56) References Cited

U.S. PATENT DOCUMENTS

| | | | |
|---|---|---|---|
| 4,911,148 A | 3/1990 | Sosnowski et al. | |
| 5,676,653 A | 10/1997 | Taylor | |

(Continued)

FOREIGN PATENT DOCUMENTS

| | | |
|---|---|---|
| JP | 2005305185 | 11/2005 |
| JP | 2012070882 | 4/2012 |

OTHER PUBLICATIONS

DIN ISO 7619-1. Rubber, vulcanized or thermoplastic—Determination of indentation hardness—Part 1: Durometer method (Shore hardness) (ISO 7619-1:2010) English translation of DIN ISO 7619-1:2012-02. Feb. 2012.
(Continued)

*Primary Examiner* — Kevin C Sirmons
*Assistant Examiner* — Alexandra Lalonde

(57) ABSTRACT

The presence of the pull wire ring in the distal end portion leads to limited functionality of the distal end of a steerable medical device. A steerable medical device (1) includes a pull wire ring (100*a-e*) for imparting a bending movement on the steerable medical device. By providing the pull wire ring (100*a-e*) with an eccentric recess (105*a-f*) which defines a passage between a first end face (101) and a second end face (105) of the ring, it becomes possible to guide ancillary elements such as electrical lines, data cables and fiber optics past the pull wire ring (100*a-e*) further towards the distal end
(Continued)

of the steerable medical device. By this measure, functionality of the distal end of the medical device is enhanced without obstructing a main lumen of the device.

20 Claims, 4 Drawing Sheets

(58) Field of Classification Search
CPC ... A61B 18/1492; A61B 1/0051; A61B 1/005; A61B 1/0055; A61B 1/008; A61B 2017/003; A61B 2017/00292; A61B 2017/00327; A61B 2017/00314; A61B 17/00234; A61M 25/0147; A61M 25/0133; A61M 25/01; A61M 25/0105; A61M 2025/015; A61M 2025/0166; A61M 25/0158; A61M 25/09
See application file for complete search history.

(56) References Cited

U.S. PATENT DOCUMENTS

| | | |
|---|---|---|
| 8,273,073 B2 | 9/2012 | Levine et al. |
| 2005/0288656 A1 | 12/2005 | Koerner et al. |
| 2010/0168666 A1 | 7/2010 | Tegg |
| 2012/0078076 A1* | 3/2012 | Stewart .............. A61B 18/1492 600/373 |
| 2012/0330230 A1 | 12/2012 | Potter |
| 2014/0148673 A1 | 5/2014 | Bogusky |
| 2014/0194814 A1 | 7/2014 | Benscoter et al. |
| 2014/0257130 A1* | 9/2014 | Cao ................... A61B 18/1492 600/549 |
| 2014/0309661 A1* | 10/2014 | Sheps .............. A61M 25/0147 606/130 |
| 2015/0272734 A1 | 10/2015 | Sheps et al. |

OTHER PUBLICATIONS

Designation: D2240-05 (Reapproved 2010). "Standard Test Method for Rubber Property-Durometer Hardness". ASTM International.
DIN EN ISO 868 "Plastics and ebonite. Determination of indentation hardness by means of a durometer (Shore hardness)". Oct. 2003.

* cited by examiner

STEERABLE MEDICAL DEVICE, AND USE OF A PULL WIRE RING THEREIN

CROSS-REFERENCE TO PRIOR APPLICATIONS

This application is the U.S. National Phase application under 35 U.S.C. § 371 of International Application Serial No. PCT/EP2015/075660, filed on Nov. 4, 2015, which claims the benefit of European Patent Application No. 14191734.4, filed on Nov. 4, 2014. This application is hereby incorporated by reference herein.

FIELD OF THE INVENTION

The invention relates to a steerable medical device, in particular a catheter or sheath. The invention further relates to the use of a pull wire ring in a steerable medical device of the aforementioned type.

BACKGROUND OF THE INVENTION

It is generally known in the art to impart a bending movement onto the distal end portion of a steerable medical device such as a catheter or sheath by using one or more pull wires. The pull wires are attached to the distal end portion of the steerable device by means of pull wire rings, sometimes also referred to as control rings, which in turn are fixed to the medical device.

WO 2014/064 694 A2, U.S. Pat. No. 8,273,073 B2, US 2014/0148673 A1, US 2014/0194814 A1, US 2005/0288656 A1, disclose and exemplarily describe the use of conventional pull wire rings in steerable medical devices such as catheters. Pull wire rings known in the art often comprise a central main lumen. The main lumen has a clearance essentially being adapted to the clearance of the main lumen of the catheter and can be used for various purposes such as accommodating instruments or diagnostic tools, or for transporting fluids. This main lumen is in certain applications not available for hosting additional conductor lines such as electric cables, data cables or fiber optics. When installing these ancillary elements in the device wall the ancillary elements terminate at the pull wire ring in the distal end region.

US 2012/0078076 A1 discloses a steerable medical device having a pull wire ring in a distal end portion of the device. The ring comprises an excentric recess in which a pull wire terminates. A number of wires are passed through a central lumen of the device.

SUMMARY OF THE INVENTION

The central disadvantage discovered in the prior art is that those ancillary elements cannot be led past the pull wire ring forwarding the distal end directly, which limits the functionality and effectiveness of the steerable medical device as a whole.

It is an object of the invention to provide a steerable medical device, in particular a catheter, sheath or guide wire with enhanced functionality.

It is a further object of the invention to provide a use of a pull wire ring in a steerable medical device, such as a catheter, sheath or guide wire, with enhanced functionality.

In a first aspect of the present invention, a steerable medical device, in particular a catheter, sheath or guide wire is presented, the device comprising a device body, said device body defining a main lumen, at least one pull wire extending from a proximal end portion of the device towards a distal end portion of the device, and a pull wire ring located in the distal end portion of the device, said pull wire being attached to the pull wire ring and adapted to impart a bending movement to the device, wherein the pull wire ring used in the steerable medical device comprises a first end face and a second end face opposite of the first end face, an outer peripheral surface and an inner peripheral surface respectively extending between the first and second end face, fixation means for attaching at least one pull wire, preferably two or more, pull wires to the ring, and further comprising at least one eccentric recess extending from the first end face to the second end face, said recess defining a passage for at least one ancillary element.

The steerable device comprises at least one ancillary element extending through the eccentric recess of the pull wire ring and from the pull wire ring further towards the distal end of the device.

It is a central benefit of the invention that the eccentric recess provided in the ring allows for the installation of ancillary elements also past the pull wire ring towards the distal end of the steerable medical device without obstructing the main lumen of the device. Similar to guide wires, it has been found that with the novel pull wire ring, ancillary wiring can be installed in the wall of the steerable medical device and led past the pull wire ring through the eccentric recess. Accordingly, it becomes possible to enhance the functionality of the steerable medical device in particular at the distal end, the tip, by providing additional technical functions there, which may require amongst others electric power supply, or data transmission e.g. through data cables or optic fibers.

Preferably, the eccentric recess is an indentation in the outer peripheral surface of the ring. This way, the recess defines an additional lumen between itself and a cavity wall of the steerable medical device at the spot where the pull wire ring is installed.

In a preferred alternative, the eccentric recess is an indentation in the inner peripheral surface of the ring. In this embodiment, the recess enhances the inner lumen defined by the inner peripheral surface by an additional lumen defined within the indentation itself.

In a further preferred alternative, the pull wire ring has a recess, which is formed as a through-hole. The through-hole may for example have a cylindrical cross-section or may be an elongate recess covering a certain angular portion inside the wall of the steerable medical device.

In a further preferred embodiment, the recess is a gap extending from the outer peripheral surface to the inner peripheral surface. In other terms, the gap opens the otherwise closed ring structure in the radial direction. The gap can either be a small slot covering only a small angular portion of the ring of e.g. less than 10°. Alternatively, the gap may however also be larger than that. The cross-sectional shape of the pull wire ring having one gap resembles a horseshoe. The horseshoe geometry is particularly useful in cases where a larger number of additional ancillary elements shall be led past the pull wire ring towards the distal end of the steerable medical device.

Hereinabove, the pull wire ring has been mainly described referring to only a singular eccentric recess. It is, however, also preferred that the ring comprises a plurality of eccentric recesses, one, several or all eccentric recesses being selected from the group consisting of: An indentation in the outer peripheral surface of the ring, an indentation in the inner peripheral surface of the ring, a through-hole, or a gap extending from the outer peripheral surface to the inner peripheral surface, or combinations thereof.

Preferably, the pull wire ring comprises a support structure which is attached to the ring. The support structure provides additional rigidity for the pull wire ring to withstand the forces imparted thereon during operation of the steerable medical device. In an embodiment wherein the ring comprises one or more gaps extending from the outer peripheral surface to the inner peripheral surface it is particularly beneficial to strengthen the structure of the ring with said support structure. Preferentially, the support structure at least partially embeds the ring.

When a support structure is provided, preferably the at least one eccentric recess extends through the support structure.

The support structure preferably consists of a polymer material having a Shore durometer of 50D or higher. The Shore durometer is for example determined in standardized analyses. Known standards describing the Shore durometer analysis include DIN EN ISO 868, DIN ISO 7619-1 or ASTM D2240.

The support structure preferably is made of an elastomer. The polymer may in preferred embodiments be a thermoplastic. Specifically, it is preferred if the material is selected from the list consisting of polyurethane, polyethylene, polyvinyl chloride, polyether block amide (Pebax), polyether ether ketone (PEEK), polyamide, thermosetting polymer, shrink tubing, in particular fluorinated ethylene propylene (FEP), polyester, or combinations thereof.

The ancillary element which can be led through the eccentric recess preferably is selected from the list consisting of: Electric lines, data cables, fiber optics, or combinations thereof.

In a second aspect, a use of a pull wire ring for imparting a bending movement onto a distal end portion of a steerable medical device is presented, wherein at least one ancillary element is passed past the pull wire ring towards the distal end of the device, wherein the pull wire ring is formed according to any one of the preferred embodiments described hereinabove.

In a third aspect, the invention relates to a pull wire ring for use in a steerable medical device, in particular a catheter, sheath or a guide wire.

It is an object of the invention according to the third aspect to provide a pull wire ring for use in a steerable medical device, in particular a catheter, sheath, or guide wire, which enhances the functionality of the steerable medical device.

In this third aspect, a pull wire ring for use in a steerable medical device, in particular a catheter, sheath or guide wire is presented, the ring being formed in accordance with any one of the embodiments described hereinabove. In particular, the pull wire ring comprises a first end face and a second end face opposite the first end face, an outer peripheral surface and an inner peripheral surface respectively extending between the first and second end face, and fixation means for attaching at least one, preferably two or more, pull wires to the ring, wherein the ring further comprises at least one eccentric recess extending from the first end face to the second end face, said recess defining a passage for at least one ancillary element. Under opposite, in terms of the present invention, it is understood that one of the two end faces of the ring is generally oriented towards the proximal end of the medical device, when installed, while the other end face is generally oriented facing the distal end of the medical device, when installed.

It shall further be understood that a preferred embodiment of the invention can also be any combination of the dependent claims with the respective independent claim. These and other aspects of the invention will be apparent from and elucidated with reference to the embodiments described hereinafter.

DETAILED DESCRIPTION OF EMBODIMENTS

Figure 1:
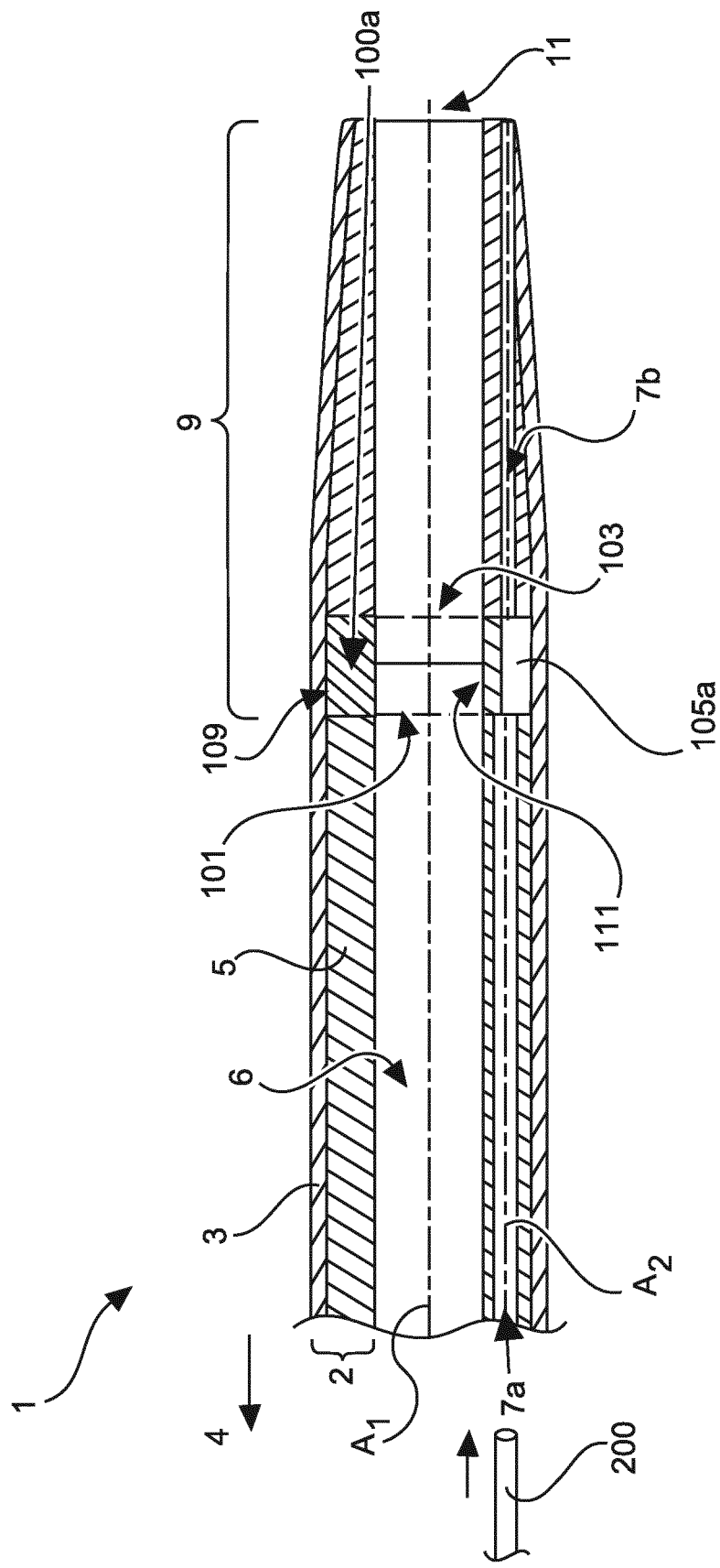
FIG. 1 schematically and exemplarily shows a steerable medical device according to a first embodiment, FIG. 2A schematically and exemplarily shows a pull wire ring according to a first embodiment, FIG. 2B schematically and exemplarily shows a pull wire ring according to a second embodiment, FIG. 2C schematically and exemplarily shows a pull wire ring according to a third embodiment, FIG. 2D schematically and exemplarily shows a pull wire ring according to a fourth embodiment, and FIG. 3 schematically and exemplarily shows a cross sectional view through a steerable medical device having a pull wire ring according to a fifth embodiment.

FIG. 1 depicts a steerable medical device 1. The device 1 comprises an outer wall 3 and an inner wall 5 which is encompassed by the outer wall 3. The device 1 comprises a device body 2, a main lumen 6 and an eccentrically located ancillary lumen 7a, 7b.

The device 1 comprises a proximal portion 4, and a distal end portion 9 terminated by a tip 11. In the distal end portion 9, a pull wire ring 100a according to a first embodiment is installed. Alternatively, any one of the pull wire rings 100b-e of the further preferred embodiments could be installed, as well. The pull wire ring 100a comprises a first end face 101 facing away from the distal end portion 9 and a second end face 103 facing the distal end or tip 11 of the device 1. The pull wire ring 100a further comprises an outer peripheral surface 109 which abuts against the outer wall 3 of device 1. Furthermore, the pull wire ring 100a comprises an inner peripheral surface 111 which has a clearance which is preferably equal to or larger than the clearance of the main lumen 6. In the arrangement of FIG. 1, the pull wire ring 100a is oriented substantially coaxially with respect to axis A1.

A recess 105a is formed in the outer peripheral surface 109 of pull wire ring 100a. Recess 105a defines a passage between the ring 100a and the wall of the device 1, said passage allowing transfer of an ancillary element 200 from ancillary lumen 7a through to ancillary lumen 7b.

Ancillary lumen 7b is depicted in FIG. 1 as extending entirely through to the distal end or tip 11, but could within the scope of the invention terminate anywhere between the pull wire ring 100a and tip 11, depending on where the added functionality shall exactly be provided.

Figure 2A:
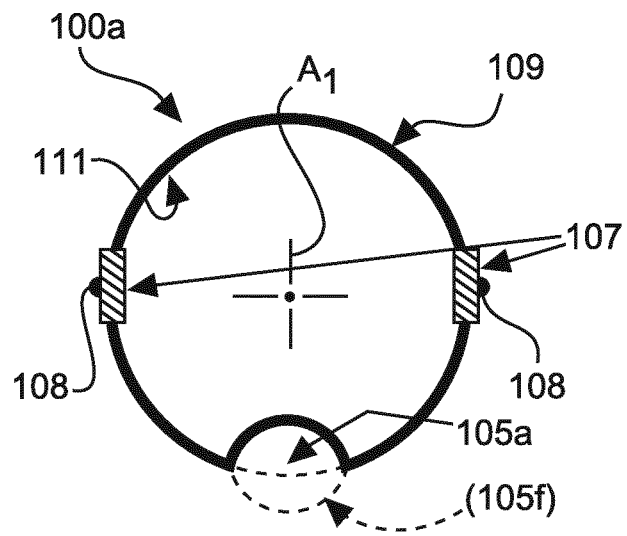

The pull wire ring 100a shown in FIG. 1 is also depicted in a schematic cross-sectional view in FIG. 2A. In addition to the features also shown in FIG. 1, the pull wire ring 100a further comprises fixation means 107 for attaching pull wires to the ring 100a. The fixation means 107 may comprise mechanical coupling means which allow an interlocking relationship between the pull wires and the pull wire ring 100a. Alternatively or additionally, the fixation means 107 may comprise a material portion which allows for permanently attaching the pull wires 108 to the pull wire ring 100a, such as by way of welding, soldering, knotting or gluing.

As is shown in FIG. 2A, recess 105a is formed as an indentation from the outer peripheral surface 109 inwards. Alternatively, a recess 105f could also be formed as an indentation from the inner peripheral surface 111 outwards, as indicated by the crossed lines in FIG. 2A.

In the ensuing description of FIGS. 2B through D and 3, identical reference signs are used for identical elements. With regard to those elements, reference is made to the description of FIGS. 1 and 2A herein above.

Figure 2B:
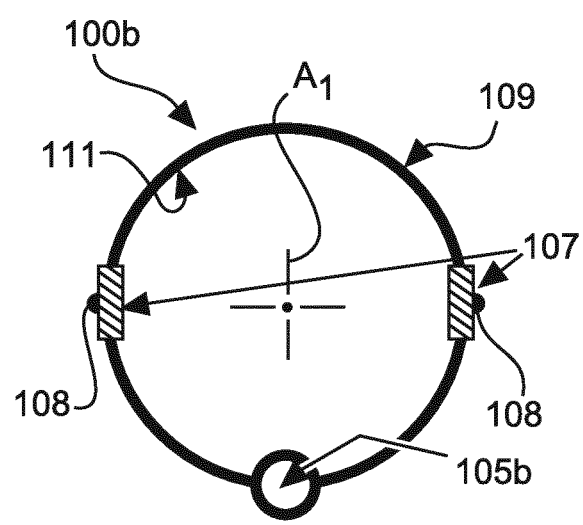

FIG. 2B depicts a variant of a pull wire ring 100b. The pull wire ring 100b could alternatively be used in the medical device 1 of FIG. 1. Instead of an indentation, the pull wire ring 100b comprises a recess in the form of a through-hole 105b. The through-hole 105b in the embodiment of FIG. 2B has a circular cross-section. However, different cross-sectional geometries are also within the scope of the invention, as is for example shown with respect to FIG. 3 (see below).

Figure 2C:
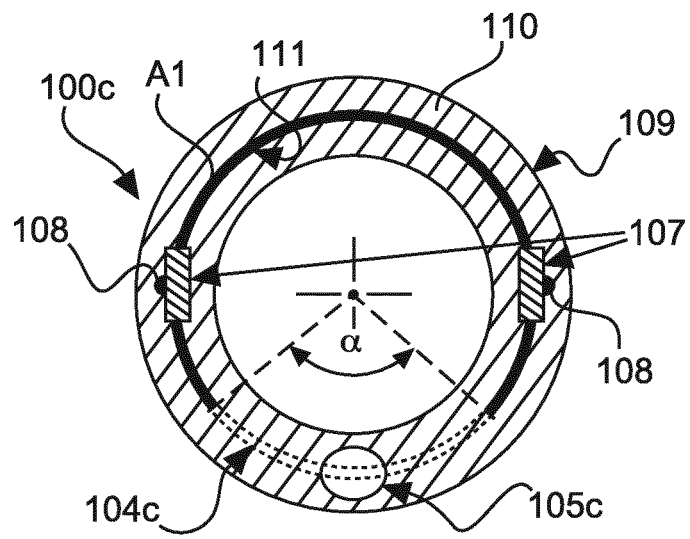

While the embodiments of pull wire rings 100a and 100b show ring geometries with closed circumferential surfaces, FIG. 2C shows as a further variant a pull wire ring 100c with an open circumferential geometry. Instead of an indentation or through-hole, pull wire ring 100c comprises a gap 104c. The gap 104c extends from the outer peripheral surface 109 through to the inner peripheral surface 111 and creates an opening across an angle α. The larger the angle α, the larger is the passage which is defined between the two gap ends. The pull wire ring 100c of FIG. 2C thus would have horseshoe geometry if it were not fully embedded in a support structure 110. Preferably, as shown in FIG. 2C, the pull wire ring 100c comprises a support structure 110. An eccentric recess in the form of a through-hole 105c is preferably formed in and extends through the support structure 110. In embodiments without a support structure, the gap 104c would constitute the eccentric recess which defines a passage for at least one ancillary element.

Figure 2D:
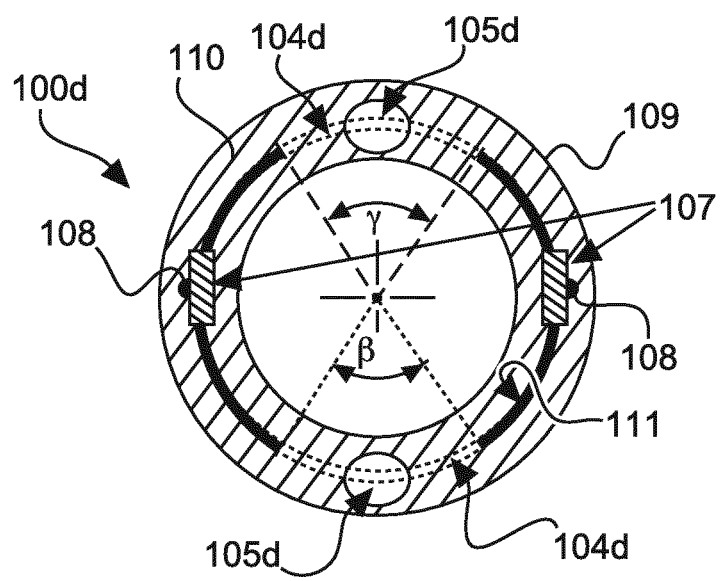

In a further embodiment, FIG. 2D shows a segmented pull wire ring 100d. The segmented pull wire ring 100D comprises not one, but two gaps 104d, respectively extending from the outer peripheral surface 109 through to the inner peripheral surface 111. The gaps span over angles β and γ, respectively. In the depicted embodiment, β is equal to γ. The segments of the pull wire ring 100d are either fixed independently from each other to the inner walls of the device 1 of FIG. 1, or, preferably and as shown in FIG. 2D, are embedded in the support structure 110 for increased stability. Inside the gaps 104d, two eccentric recesses in the form of through-holes 105d are formed in and extend through the support structure 110.

Figure 3:
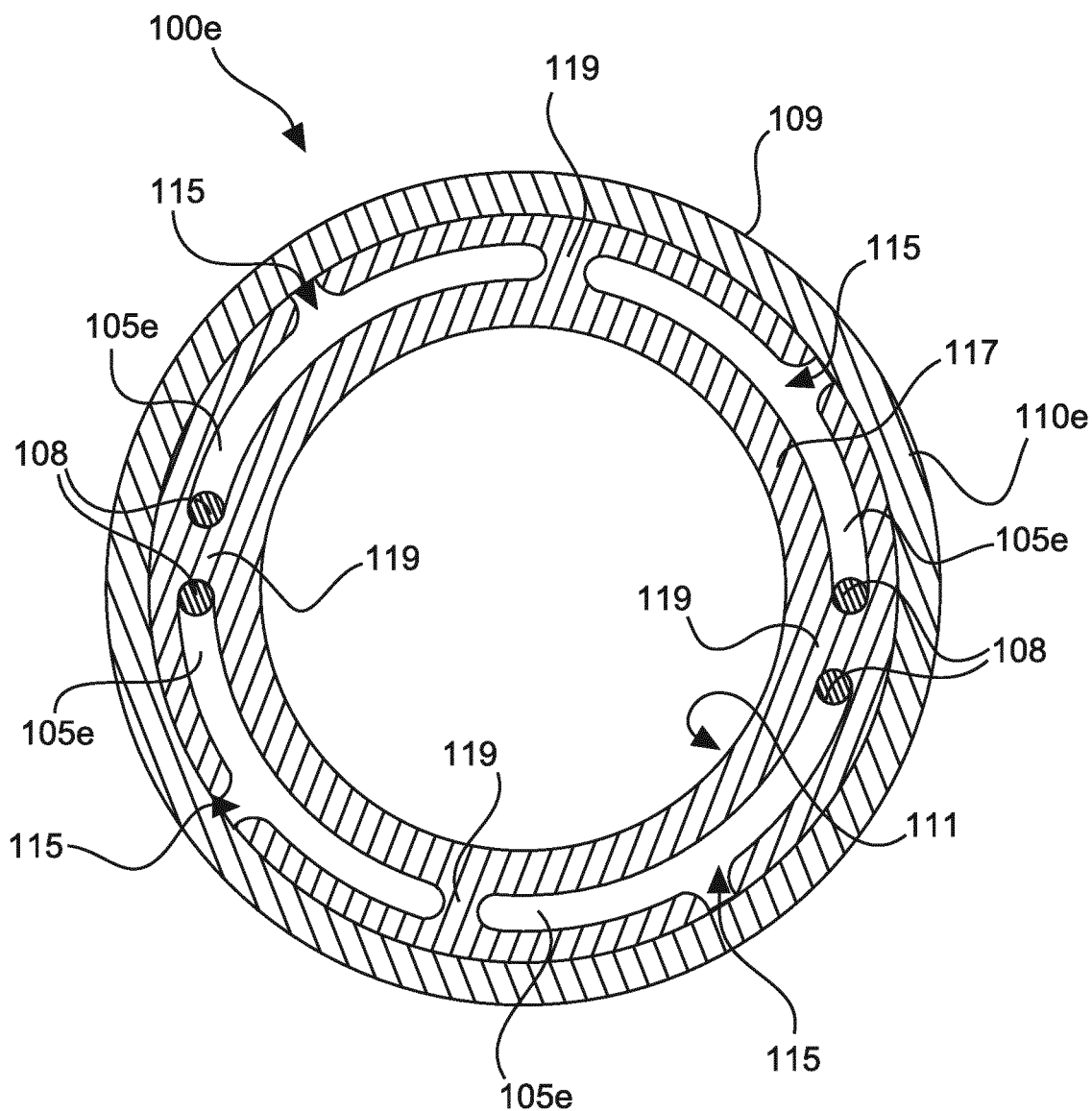

FIG. 3 shows a further embodiment of a pull wire ring 100e in accordance with the invention. The pull wire ring 100e is shown with a support structure 110e, extending around a base body 117. The support structure 110e may be a shrink-fit tube or conventional polymer material according to one of the preferred embodiments described hereinabove and defines the outer peripheral surface 109.

The pull wire ring 100e comprises a plurality of eccentric recesses 105e. The eccentric recesses 105e are formed inside the base body 117.

If the pull wire ring 100e is used in an embodiment without the support structure 100e around it, the recesses 105e are to be considered as indentations respectively having an opening 115. Otherwise, the recesses 105e are to be considered as through-holes in terms of the invention.

The pull wire ring 100e further comprises a plurality of ribs 119. The ribs 119 are adapted for holding pull wires 108. Preferably, the pull wires 108 are bent around the ribs 119 as shown in FIG. 3. The embodiment shown in FIG. 3 is particularly suited for use with polymeric pull wires, for example made of polyethylene or ultra-high-molecular-weight polyethylene (UHMW-PE). In particular, the embodiment is suited for use with Dyneema pull wires.

The pull wires 108 may be inserted into the pull wire ring 100e through to the openings 115 when the pull wire ring 100e is used without support structure 110e, or prior to mounting the support structure 100e onto the base body 117.

In the above description of the invention, a steerable medical device has been generally described. According to preferred embodiments of the invention, in particular a steerable catheter or sheath may be used as specific example of a steerable medical device.

Other variations to the disclosed embodiments can be understood and effected by those skilled in the art and practicing the claimed invention, from a study of the drawings, the disclosure and the appended claims.

In the claims, the word "comprising" does not exclude other elements or, and the indefinite article "a" or "an" does not exclude a plurality.

A single unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

If in this document the wording "and/or" is used, it is understood that one of the elements, or several or all of the elements are to be selected.

The invention claimed is:

1. A steerable medical device, comprising:
   a device body, said device body defining a main lumen,
   a pull wire extending from a proximal end portion of the device towards a distal end portion of the device, and
   a pull wire ring located in the distal end portion of the device, said pull wire being attached to the pull wire ring and adapted to impart a bending movement to the device,
   wherein the pull wire ring comprises:
      a first end face and a second end face opposite of the first end face,
      an outer peripheral surface and an inner peripheral surface respectively extending between the first and second end face,
      an eccentric recess extending from the first end face to the second end face, the eccentric recess defining a passage configured to receive an ancillary element selected from the group of electric lines, data cables and fiber optics; and
   wherein the pull wire is attached to the pull wire ring circumferentially displaced from the eccentric recess;
   the steerable device further comprising the ancillary element extending through the eccentric recess of the pull wire ring into the distal end portion of the device.

2. The steerable medical device of claim 1, wherein the eccentric recess is an indentation in the outer peripheral surface of the pull wire ring.

3. The steerable medical device of claim 1, wherein the eccentric recess is an indentation in the inner peripheral surface of the pull wire ring.

4. The steerable medical device of claim 1, wherein the eccentric recess of the pull wire ring is a through-hole.

5. The steerable medical device of claim 1, wherein the eccentric recess of the pull wire ring is a gap extending from the outer peripheral surface to the inner peripheral surface.

6. The steerable medical device of claim 1, wherein the pull wire ring comprises:
   a plurality of eccentric recesses, and
   one, several or all of the plurality of eccentric recesses being selected from the group consisting of:
      an indentation in the outer peripheral surface of the pull wire ring,
      an indentation in the inner peripheral surface of the pull wire ring,
      a through-hole,
      a gap extending from the outer peripheral surface to the inner peripheral surface.

7. The steerable medical device of claim 1, comprising a support structure which is attached to the pull wire ring.

8. The steerable medical device of claim 7, wherein the support structure at least partially embeds the pull wire ring.

9. The steerable medical device of claim 7, wherein the eccentric recess extends through the support structure of the pull wire ring.

10. The steerable medical device of claim 7, wherein the support structure of the pull wire ring consists of a polymer material having a Shore durometer of 50D or higher.

11. The steerable medical device of claim 7, wherein the support structure of the pull wire ring is made of at least one of the following:
    an elastomer,
    a thermoplastic,
    polyurethane,
    polyethylene,
    polyvinyl chloride,
    polyether block amide,
    polyether ether ketone,
    polyamide,
    a thermosetting polymer,
    a shrink tubing,
    fluorinated ethylene propylene,
    polyester,
    or combinations thereof.

12. The steerable medical device of claim 1, wherein the main lumen defined by the device body extends from the proximal end portion of the device to the distal end portion of the device and wherein the device body further defines an eccentrically located ancillary lumen extending from the proximal end portion of the device to the eccentric recess of the pull wire ring and from the eccentric recess to the distal end portion of the device.

13. The steerable medical device of claim 12, wherein the ancillary element extends through a proximal end portion of the eccentrically located ancillary lumen, the eccentric recess defined in the pull wire ring, and a distal end portion of the eccentrically located ancillary lumen.

14. The steerable medical device of claim 13, wherein the distal end portion of the eccentrically located ancillary lumen extends from the eccentric recess of the pull wire ring to a distal end of the device body.

15. A steerable medical device comprising:
    a device body, said device body defining a main lumen extending from a proximal end portion of the device body to a distal end portion of the device body and an eccentrically located ancillary lumen extending from the proximal end portion of the device body to the distal end portion of the device body;
    a pull wire extending from the proximal end portion of the device body towards the distal end portion of the device body; and
    a pull wire ring located in the distal end portion of the device body, said pull wire being attached to the pull wire ring and adapted to impart a bending movement to the device body, the pull wire ring including:
       a first end face and a second end face opposite of the first end face,
       an outer peripheral surface and an inner peripheral surface respectively extending between the first end face and the second end face,
       an eccentric recess extending from the first end face to the second end face in alignment with the eccentrically located ancillary lumen, said eccentric recess defining a passage through the pull wire ring between the first and second end faces, wherein the pull wire is attached to the pull wire ring circumferentially displaced from the eccentric recess;
    at least one ancillary element extending through a proximal end portion of the eccentrically located ancillary lumen, through the eccentric recess of the pull wire ring, and into the distal end portion of the device body, the at least one ancillary element including at least one of electric lines, data cables, and fiber optics.

16. The steerable medical device of claim 15, wherein the eccentrically located ancillary lumen extends through the distal end of the device body.

17. The steerable medical device of claim 15, wherein the eccentric recess of the pull wire ring is a gap extending from the outer peripheral surface to the inner peripheral surface.

18. The steerable medical device of claim 15, wherein the pull wire ring comprises:
    a plurality of eccentric recesses, and
    one or more of the plurality of eccentric recesses being selected from the group consisting of:
       an indentation in the outer peripheral surface of the pull wire ring,
       an indentation in the inner peripheral surface of the pull wire ring,
       a through-hole,
       a gap extending from the outer peripheral surface to the inner peripheral surface.

19. The steerable medical device of claim 15, further including a peripheral support structure extending peripherally around the pull wire ring, the support structure defining the eccentric recess therethough.

20. A method of using a steerable medical device which steerable medical device includes:
    a device body, said device body defining a main lumen extending from a proximal end portion of the device body to a distal end portion of the device body and an eccentrically located ancillary lumen extending from the proximal end portion of the device body to the distal end portion of the device body;
    a pull wire extending through the proximal end portion towards the distal end portion; and
    a pull wire ring located in the distal end portion of the device body, said pull wire being attached to the pull wire ring and configured to impart a bending movement to the distal end portion of the device body, the pull wire ring including:
       a first end face and a second end face opposite of the first end face,
       an outer peripheral surface and an inner peripheral surface respectively extending between the first end face and the second end face, an eccentric recess extending from the first end face to the second end face in alignment with the eccentrically located ancillary lumen, said eccentric recess defining a passage through the pull wire ring between the first and second end faces, the pull wire being attached to the pull wire ring circumferentially displaced from the eccentric recess;

THE METHOD COMPRISING:

passing an ancillary element through a proximal end portion of the eccentrically located ancillary lumen through the eccentric recess of the pull wire ring, and through the distal end portion of the eccentrically located ancillary lumen, the ancillary element including at least one of electric lines, data cables, and fiber optics; and pulling the pull wire to steer the distal end portion of the device body.

\* \* \* \* \*